United States Patent [19]

Raymond et al.

[11] Patent Number: 5,079,951
[45] Date of Patent: Jan. 14, 1992

[54] ULTRASONIC CARCASS INSPECTION

[75] Inventors: Donald P. Raymond; Eugene J. Brach, both of Nepean, Canada

[73] Assignee: Her Majesty the Queen in right of Canada, as represented by the Minister of Agriculture, Ottawa, Canada

[21] Appl. No.: 568,475

[22] Filed: Aug. 16, 1990

[51] Int. Cl.$^5$ .................. G01N 29/06; G01N 29/18; G01N 29/20
[52] U.S. Cl. ............................ 73/602; 128/660.07; 128/660.09; 73/597; 73/599; 73/619
[58] Field of Search .............. 73/597, 599, 602, 619, 73/620, 621, 629; 128/660.07, 660.09

[56] References Cited

U.S. PATENT DOCUMENTS 4,553,437 11/1985 Luthra et al. .................. 73/602
4,651,567 3/1987 Sandhu ........................ 73/621

FOREIGN PATENT DOCUMENTS 2213263 8/1989 United Kingdom .............. 73/599

Primary Examiner—Hezron E. Williams
Assistant Examiner—Rose M. Finley

[57] ABSTRACT

A meat carcass is inspected ultrasonically to determine its fat-to-lean ratio and to obtain a three-dimensional computer image of the interior of the carcass showing the location, shape and nature of the various pixels of different materials, (fat, lean, and possibly also bone, abscesses or other tissues) in the carcass. These results are achieved by passing ultrasonic pulses into and through the carcass, measuring the timing of both transmitted pulses and return pulses that are reflected from the carcass surfaces and from successive planes between the internal pixels, and measuring the relative intensities of the reflected pulses, the latter measurement providing data on the attenuation coefficients of the various pixels from which their nature can be determined. The velocities of the ultrasonic pulses in the different materials being known, as well as their attenuation coefficients, a computer can calculate the fat-to-lean ratio and can construct the desired three-dimensional image.

17 Claims, 5 Drawing Sheets

ULTRASONIC CARCASS INSPECTION

FIELD OF THE INVENTION

This invention relates to a system employing ultrasonic pulses for inspecting meat carcasses or parts thereof (hereinafter simply referred to as "carcasses").

BACKGROUND OF THE INVENTION

In most countries, including Canada, meat carcasses must by law be graded at the abattoir. The conventional methods of inspection are by the eye of an experienced inspector or by means of an electronic probe that is inserted manually into one or more sites in the carcass. These methods enables rough estimates to be obtained of the locations and relative proportions of fat and lean. Even when a probe is used, it must be operated manually, which results in inconsistancies in its placing and angle of insertion. With either of the conventional methods a substantial subjective factor is introduced into the measurements.

PRIOR ART

Sonic inspection methods have been proposed for inspecting animal carcasses. See, for example, Stouffer et al, U.S. Pat. No. 4,099,420 issued July 11, 1978 and Stouffer U.S. Pat. No. 4,785,817 issued Nov. 22, 1988. In addition, ultrasonic imaging systems have been used for examining specimens of both human and animal tissue. See, for example, Stouffer U.S. Pat. No. 3,603,303 issued Sept. 7, 1971; Hartemann et al U.S. Pat. No. 4,212,206 issued July 15, 1980; and Johnson U.S. Pat. No. 4,317,369 issued Mar. 2, 1982.

Advantages offered by ultrasonic technology over earlier equipment is that fat-to-lean ratios can be recorded, and measurements of subcutaneous and intermuscular fat depth can be obtained. A combination of subcutaneous and intermuscular fat measurements provides a more accurate estimate of total carcass fatness. Ultrasound is a non-invasive means of examining the internal structures and physical properties of biological tissue, and, since the number of measurement points is optional, a whole carcass can be measured. The measurement is fast, and the ultrasonic data can easily be transported to a computer. Data or image processing can be used to calculate different parameters, such as the velocity of the ultrasound in the tissue, attenuation, scattering, and the scattering spectrum, these being characteristics that typically identify the nature of the tissue.

During the 1980s, several researchers have been working on the application of ultrasonic technology to the measurement of meat quality. The most significant among these applications are those related to the velocity measurement of ultrasound. See (i) C. A. Miles, A. J. Fursay and R. W. R. York, 'New equipment for measuring the speed of Ultrasound and its application in the estimation of body composition of farm livestock'. In: In vivo measurement of Body Composition in Meat Animals (Ed: D. Lister) "Elsevier Applied Science" London/New York pp. 93-105. (1984); and (ii) C. A. Miles, A. V. Fisher, G. A. J. Fursey and S. J. Page, 'Estimating Beef Carcass Composition Using the Speed of Ultrasound'. "Meat. Science" 21. pp. 175-8. (1987).

In relation to the attenuation of ultrasound see (iii) J. C. Forrest, C. H. Kuei, W. Orcutt, A. P. Schinchel, J. R. Stouffer and M. D. Judge, 'Electromagnetic Scanning, Ultrasonic imaging and electronic probing for estimation of pork carcass composition'. In: Proceedings 34th International Congress of Meat Science and Technology, pp. 31. (1988);

In relation to video image analysis see (iv) P. B. Newman, 'The use of Video Image Analysis for Quantitative Measurement of Visible Fat and Lean in Meat Part 4 - Application of Image Analysis Measurement Techniques to Minced Meats'. "Meat Science 19. pp. 139-150. (1987); and (v) H. R, Cross, D. A. Gilliland, P. R. Durland and S. C. Seideman, 'Beef carcass evaluation by use of Video image analysis system'. "Journal of Animal Science" 57. pp. 908 (1983).

However, for various practical reasons none of these prior proposals has yet proved sufficiently effective to be widely adopted commercially, and there still remains a need for an improved system that can provide accurate data reliably, while reducing the highly labor intensive nature of the methods currently in use.

SUMMARY OF THE INVENTION

An object of an embodiment of the present invention is to provide a system for grading a carcass, that will furnish a reading of the fat-to-lean ratio of the whole carcass in a manner that affords more accuracy than has hitherto been obtainable.

A further object of an embodiment of the invention is to provide a system that can detect abscesses in a carcass. Subject to its size, an abscess may require complete rejection of the carcass, or at least the part of the carcass containing the abscess, thus significantly devaluing the carcass. An abscess that is buried deep in a carcass is unlikely to be detected by conventional inspection methods and hence is usually not discovered until the carcass is butchered at a later time, i.e. after the carcass has already been graded and valued.

A still further object of an embodiment of the invention is to provide a system that can detect any bone that has been left in the carcass.

Yet another object of an embodiment of the invention is to provide a system that can generate a three-dimensional computer image of the interior of a carcass, i.e. an image containing data on the location, shape and nature of various pixels of different materials (fat, lean, and possibly also bone, abscesses or other tissues) in the carcass.

A further object of the invention is to achieve the above objectives with a reduced amount of labour.

The invention consists of both improved methods of carcass inspection and improved apparatus for conducting carcass inspection.

Before describing the preferred apparatus for carrying the various aspects of the invention into practice, some theoretical explanation and definitions will be helpful.

The term AAAC has been used in the art to refer to the acoustic amplitude attenuation coefficient, i.e. the loss of energy of a sonic (usually ultrasonic) signal as it propagates through a biological medium. This attenuation coefficient will be referred to herein simply as $\alpha$. The values of $\alpha$ for the different materials typically encountered in a meat carcass for an ultrasonic signal of approximately 2 MHz at 37° C. are as follows:

| | |
|---|---|
| Fat (100%) | ≈1 dB/cm |
| Lean (100%) | ≈2 dB/cm |
| Bone | ≈20 dB/cm |
| Water | ≈0 dB/cm |
| Abscess (mainly water) | <0.5 dB/cm |
| Other tissues, e.g. connecting tissue | ≈3.5–6.0 dB/cm |

These values are approximately proportional to the ultrasonic frequency at the range of 1–5 MHz. For example, at 5 MHz the attenuation values increase to at least double the figures given above, while retaining essentially similar ratios to each other. It is the differences between these values at a selected frequency that are utilised in the present invention to distinguish between fat, lean and other materials. Although the invention can be practiced at other frequencies, a value around 2 MHz or at least somewhere between 2 and 3 MHz is a convenient and desirable frequency to adopt, because it permits effective focusing of ultrasonic signals while having lower values for the attenuation than would be observed at higher frequencies. Once the frequency has been selected, the values for $\alpha$ at this frequency will be determined in an initial calibration of the equipment using specimens the natue of which is known.

The values of $\alpha$ are also temperature sensitive, approximately doubling for a drop in temperature from 37° C. to 20° C. Since the method of the invention is carried out with the carcass immersed in a liquid, normally water, it is preferable to closely regulate the temperature of the water, e.g. to within a tolerance of no more than about 1.5° C. on each side of the selected temperature. While the invention can be practiced at other temperatures, the value of 37° C. has been chosen as the preferred value, because carcass temperatures immediately after slaughter are 36°–38° C.

Another parameter that is employed is V, the mean velocity of an ultrasonic signal in the various materials. Experiments have shown typical values for V (2 MHz at 37° C.) to be

| | |
|---|---|
| Fat (100%) | ≈1410 m/sec |
| Lean (100%) | ≈1625 m/sec |
| Bone | ≈2500 m/sec |
| Water | ≈1455 m/sec |
| Abscess (mainly water) | ≈1455 m/sec |
| Other tissues | ≈1550–1690 m/sec |

The velocity V also depends on the temperature of the material. This temperature dependence is, however, not linear, and is different in fat and lean. Hence, if an operating temperature other than 37° C. is chosen, modified values for V will need to be determined. It has been found that the curves for V for fat and lean intersect twice, around 20° C. and around −3° C. These temperatures should thus be avoided when the values of V are to be used to distinguish between fat and lean.

If the operating temperature of the water is increased above 37° C., the differential between the two values of V (for fat and lean respectively) increases somewhat, but the danger of bacterial infection increases with a rise in temperature, and normally the differential at 37° C. is sufficient for practical purposes.

All factors having thus been taken into account the value of 37° C. has been arrived at as the optional operating temperature and is hence recommended.

Although the carcass will be immersed in water when the measurements are made, the water temperature can be lower than 37° C., since the carcass is immersed for too short a time for heat transfer between it and the water to be significant.

DETAILED DESCRIPTION OF THE PREFERRED EMBODIMENTS

Figure 1:
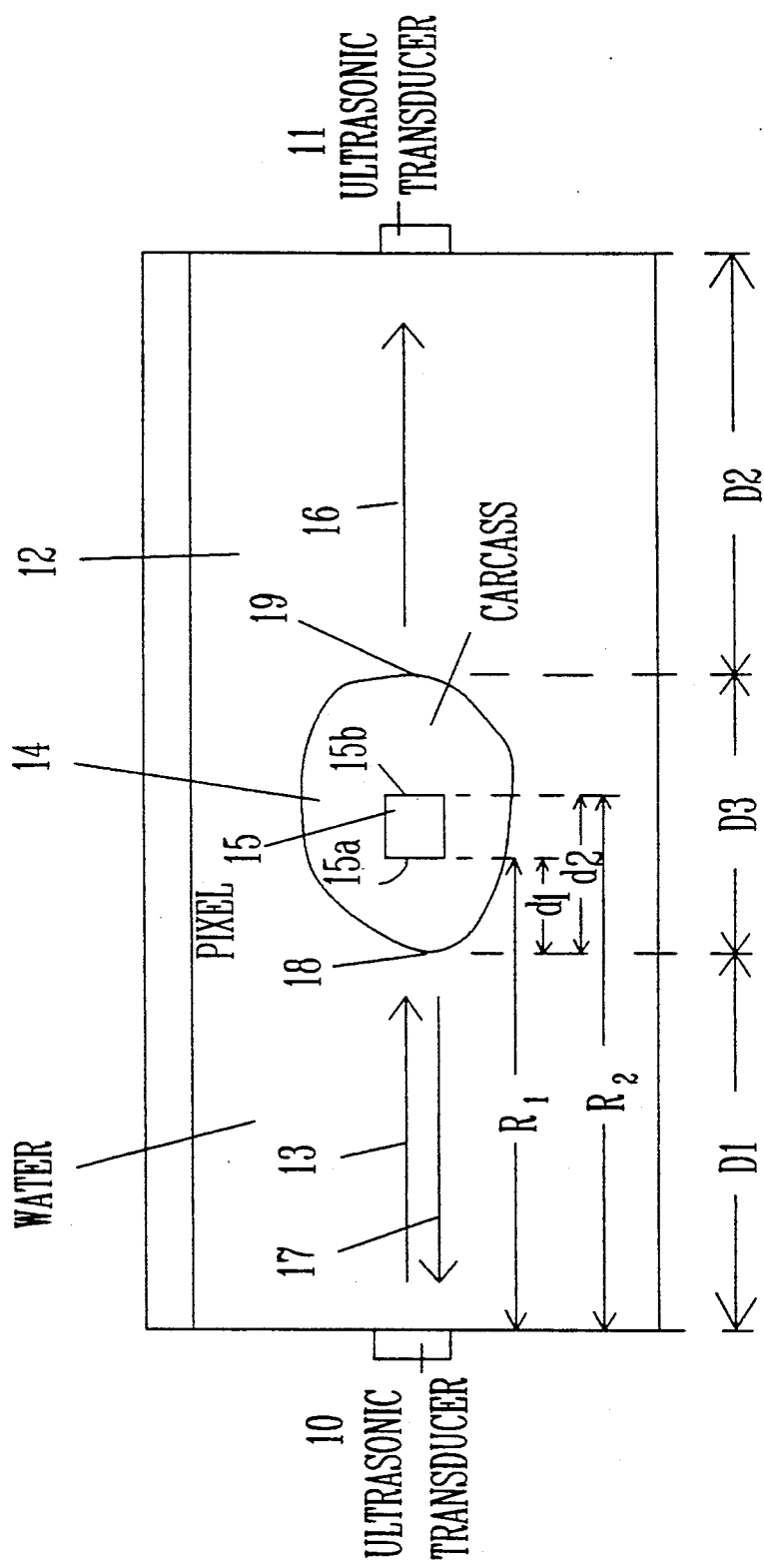
FIG. 1 is a diagram illustrating a pair of aligned ultrasonic transducers and a carcass in a tank of water between such transducers.

FIG. 1 shows diagrammatically a pair of ultrasonic transducers 10, 11 each mounted in a milar window (not shown) and aligned with each other on opposite sides of a tank 12 of liquid, normally water. A carcass 14 is positioned in the path of a focused beam 13 of ultrasonic energy, e.g. at 2 MHz, emitted by the first transducer 10 in short pulses in a first direction along a pulse axis. For the purpose of initial analysis of the system, this carcass is assumed to consist of a large number of small portions, referred to as pixels. FIG. 1 shows a representative pixel 15. A portion of the beam 13 passes through the pixel 15 (after attenuation thereby) as a transmitted beam 16 and is received by the transducer 11. The pixel 15 also returns to the transducer 10 in the reverse direction along the pulse axis echo or return pulses 17 reflected from its respective front and rear surfaces 15a and 15b. Since the beams take the form of a sequence of pulses of ultrasonic energy, the transducer 10, after emitting an initial pulse, will assume its receiving mode to detect the return pulses that are reflected first by the surface 18 of the carcass and then by the surfaces 15a, 15b of the pixel.

A number of measurements can be made.

As a first measurement a transmitted pulse 16 can be used to detect bone, as represented by a very low intensity of the pulse detected at the transducer 11 due to the high attenuation of bone.

In the absence of bone (which is the normal situation), the measurements can be used to obtain F, the volume fraction of fat in the carcass, i.e. the ratio of fat-to-lean. This value is based on the equation $$F = \frac{b}{V} + c \tag{1}$$

where b and c are constants, and V is the mean velocity of a pulse in the carcass.

Assuming that lean and fatty tissues are arranged in an arbitrary number of pixels in the carcass, the mean volume fraction of fat, F (average) is given by $$F(\text{average}) = \frac{b}{V(\text{average})} + c \tag{2}$$

where $$\frac{1}{V(\text{average})}$$

is the average transmission time that the ultrasonic energy takes to travel through the carcass, divided by the carcass thickness D3. The values for b and c will be determined by the initial calibration process.

The manner in which the carcass thickness D3 is measured will now be described. The first return pulse received by the transducer 10 will be from the surface 18 of the carcass 14, i.e. the plane between the water and the carcass. The timing of this return signal determines the distance D1 between the transducer 10 and the surface 18, since the velocity of the pulse in water is known. Using the transducer 11 in the same way, i.e. as both an emitter and a detector of reflected pulses, the corresponding distance D2 between the transducer 11 and the carcass surface at point 19 can similarly be determined. Since the total distance between the transducers is known, the thickness D3 of the carcass can be readily calculated.

By measuring the total time between emission of a pulse by the transducer 10 and receipt of the corresponding transmitted pulse by the transducer 11 (or vice versa), the portion of this total time required for transmission through the carcass can be calculated. This data, combined with the value of D3, provides a measured value for V (average) and hence gives the desired value for F (average) for the portion of the carcass (series of pixels) extending along the pulse axis joining the two transducers.

It will be understood that, in connection both with this determination of F (average) and with the other measurements explained below, there will be provision for scanning the carcass to control the operation of multiple pairs of transducers and relative movement between the carcass and the transducers, so that an F (average) value will be obtained for each of a number of parallel pulse axes distributed across the carcass in the two dimensions perpendicular to the pulse axes. These values for F (average) can then be combined to calculate the overall F (average) for the entire carcass, this being the data needed to assess the quality of the carcass and hence its grading and monetary value.

The operator will often also be interested in more detailed information about the carcass, such as knowledge of;

(a) the presence of an abscess, which could seriously limit the value of the carcass or cause it to be totally rejected, (b) the presence of bone in the carcass, and (c) the location, extent and nature of the various pixels of fat and lean and other materials in the carcass, preferably compiled in the form of a three-dimensional computer image, selected sections of which can be displayed on a monitor.

To generate this latter information it is necessary to measure the attenuation of each pixel (or series of pixels) in the carcass. The preferred method of achieving these measurements is to employ the real time narrowband amplitude technique, which estimates the amplitude of backscatter echoes as a function of depth.

A focused signal from the transducer 10 is energized with narrowband pulses and records echo amplitude data, i.e. return pulse intensities, from two different ranges along the pulse axis, thus defining two constant depth planes (pixel planes) in the carcass. The difference in intensity between two return pulses divided by twice the plane separation is an estimate of the attenuation of the material between the planes at the center frequency of the ultrasonic pulse.

The ratio between the received (return) power P(R) and the emitted power P(0) of an ultrasonic transducer is given in J. M. Reid, 'The scattering of ultrasound by tissues'. "National Bureau of Standards Special Publications" pp. 453. Washington DC. (1976), and is expressed as $$\frac{P(R)}{P(O)} = \frac{T^2 s_b A^2 e^{-4\alpha R}}{R^4 \lambda^2} \quad (3)$$

This equation is also disclosed in J. Ophir, et al "A Narrowband Pulse-Echo Technique for In Vivo Ultrasonic Attenuation Estimation" published in IEEE Transactions on Biomedical Engineering, Vol. BME-32, No. 3, March 1985, pgs. 205–211.

where

R is the distance from the transducer to the scattering plane (pixel plane), $\lambda$ is the wavelength, assuming the pulse to be monochromatic, T is the efficiency of the transducer, A is the effective aperture of the transducer, $\alpha$ is the attenuation coefficient, and $s_b$ is the backscatter cross section.

If the medium between the transducer and the returning plane is composed of an attenuating target (tissue) and a quasi-nonattenuating part (water), equation (3) can be rewritten as $$\frac{P(R)}{P(O)} = \frac{T^2 s_b A^2 e^{-4\alpha d}}{R^4 \lambda^2} \quad (4)$$

where

"d = R-W" is the portion of "R" for which the attenuation coefficient o is not zero (tissue), and W is the portion for which $\alpha$ is zero (water).

If there are two reflections at ranges $R_1$ and $R_2$ respectively, i.e. the near and far surfaces of a pixel, such as the surfaces 15a and 15b in FIG. 1, both having the same value for $s_b$, then the ratio of the received power from the two ranges is:

$$\frac{P(R_1)}{P(R_2)} = \frac{R_2^4}{R_1^4} \cdot e^{4\alpha(d_2 - d_1)} \quad (5)$$

where $d_1 = R_1 - W$ and $d_2 = R_2 - W$.

This equation contains the desired attenuation coefficient $\alpha$ for the material between ranges $R_1$ and $R_2$, e.g. the material of the pixel 15.

Elimination of the differences between the two R's is done in two steps:

1. Data are acquired from a given range, $R = R_1 = R_2$.

2. If the transducer were to be moved axially in the water by a known amount $(d_2 - d_1)$ and data would again be taken at the same range R from the transducer, but now at a new depth in the target, i.e. if $R_1$ and $R_2$ are equal, but $d_1$ and $d_2$ are not, then equation 5 becomes $$\frac{P(d_1)}{P(d_2)} = e^{4\alpha(d_2 - d_1)} \quad (6)$$

Because P is proportional to the square of the received voltage, referred to subsequently as the intensity I of the return pulse, solving for $\alpha$ in dB/cm, yields:

$$\alpha = 1.15 \frac{\log I(d_1) - \log I(d_2)}{d_2 - d_1} \qquad (7)$$

Generalizing equation 7 by assuming that measurements are made on many independent planes, the attenuation coefficient $\alpha$ of the tissue material becomes:

$$\alpha \propto \frac{\log I(\text{average}, d_1) - \log I(\text{average}, d_2)}{d_2 - d_1} \qquad (8)$$

The equal sign and the constant 1.15 of equation (7) have been replaced by the proportionality sign in equation (8).

By using this equation (8) as an algorithm in the computer it is possible to calculate the various measured values of $\alpha$ for the respective pixels that are distributed throughout the carcass in three dimensions. By comparing these calculated values with the known values for the respective materials, it is possible to identify the material of each pixel, i.e. whether fat, lean, bone, abscess or other tissue, and hence to compile in the computer a three-dimensional image of the carcass. A chosen two-dimensional slice of this image can then be displayed on a screen, using, for example, different colors for the respective materials. On the other hand, such a visual display is not essential. The computer can simply be instructed, for example, to signal the existence of an abscess larger than a certain size, for rejection of the carcass without the need to subject it to further visual inspection. Alternatively, the computer can be commanded to report to the operator any other characteristic of the three-dimensional computer image (and hence of the carcass) that the operator has indicated to be of particular interest.

Figure 2:
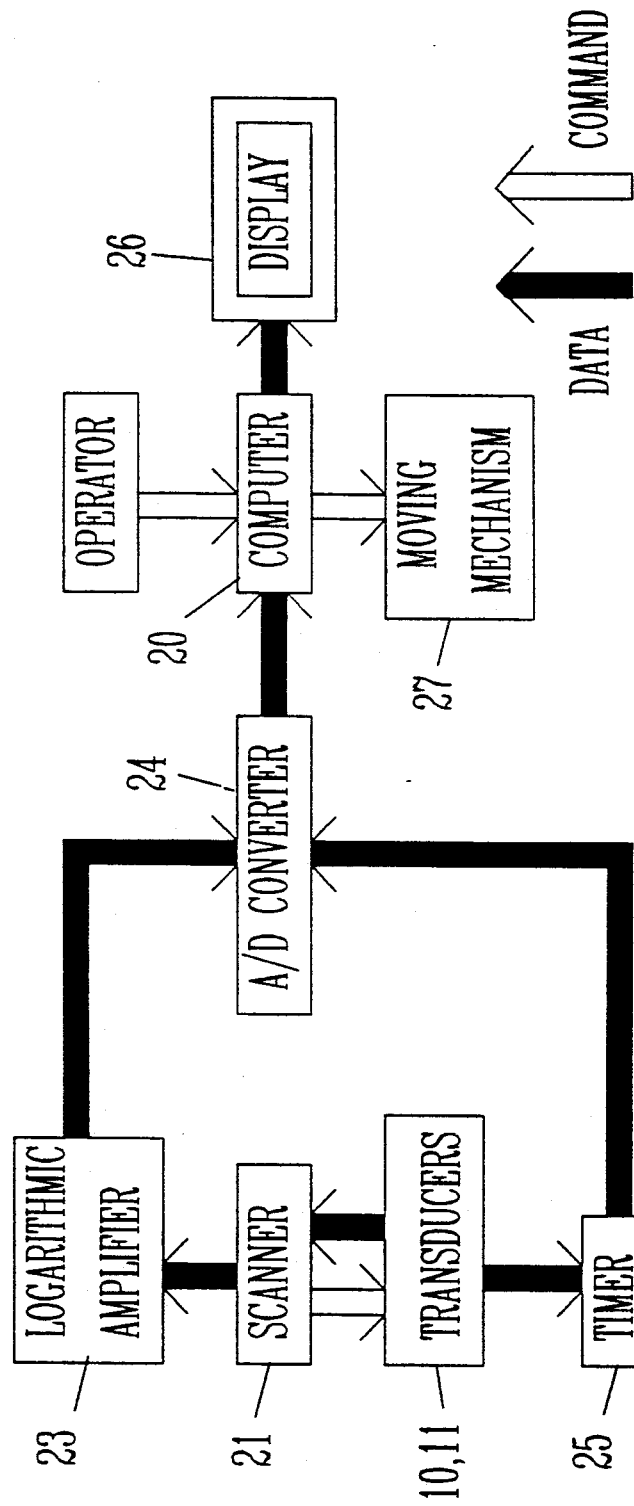
FIG. 2 is a simplified block circuit diagram.

In a preferred embodiment of the invention, the transducers 10, 11 are energized by an oscillator in a scanner 21 (FIG. 2) operated at a nominal center frequency of 2 MHz. The ultrasonic pulse energy is preferably not less than 250 mW/cm$^2$, and each transducer element is no more than 19 mm in diameter. The transducers should preferably have no more than 25% (about 0.8 MHz) fractional bandwidth (with 6 dB).

The timing of the pulses emitted by the transducers 10, 11 is controlled by the scanner 21. The detected signals (both transmitted through the carcass and reflected thereby) are fed through the scanner 21 into a logarithmic amplifier 23 and sampled at a rate of preferably not less than 10 MHz by a not less than 10-bit flash A/D converter 24 and interfaced to the computer 20.

On a signal from a timer 25, the mean velocity V of the ultrasonic signal and hence the ratio F is calculated as explained above. The attenuation $\alpha$ is also calculated from the return signal intensities, pixel by pixel, and, after image processing, the computer can display pictures of each cross-section of the carcass in colour on a display 26. If abscesses are present, these can be displayed with the computer giving the location and size of each abscess. The computer 20 also controls a moving mechanism 27 described below.

Figure 3:
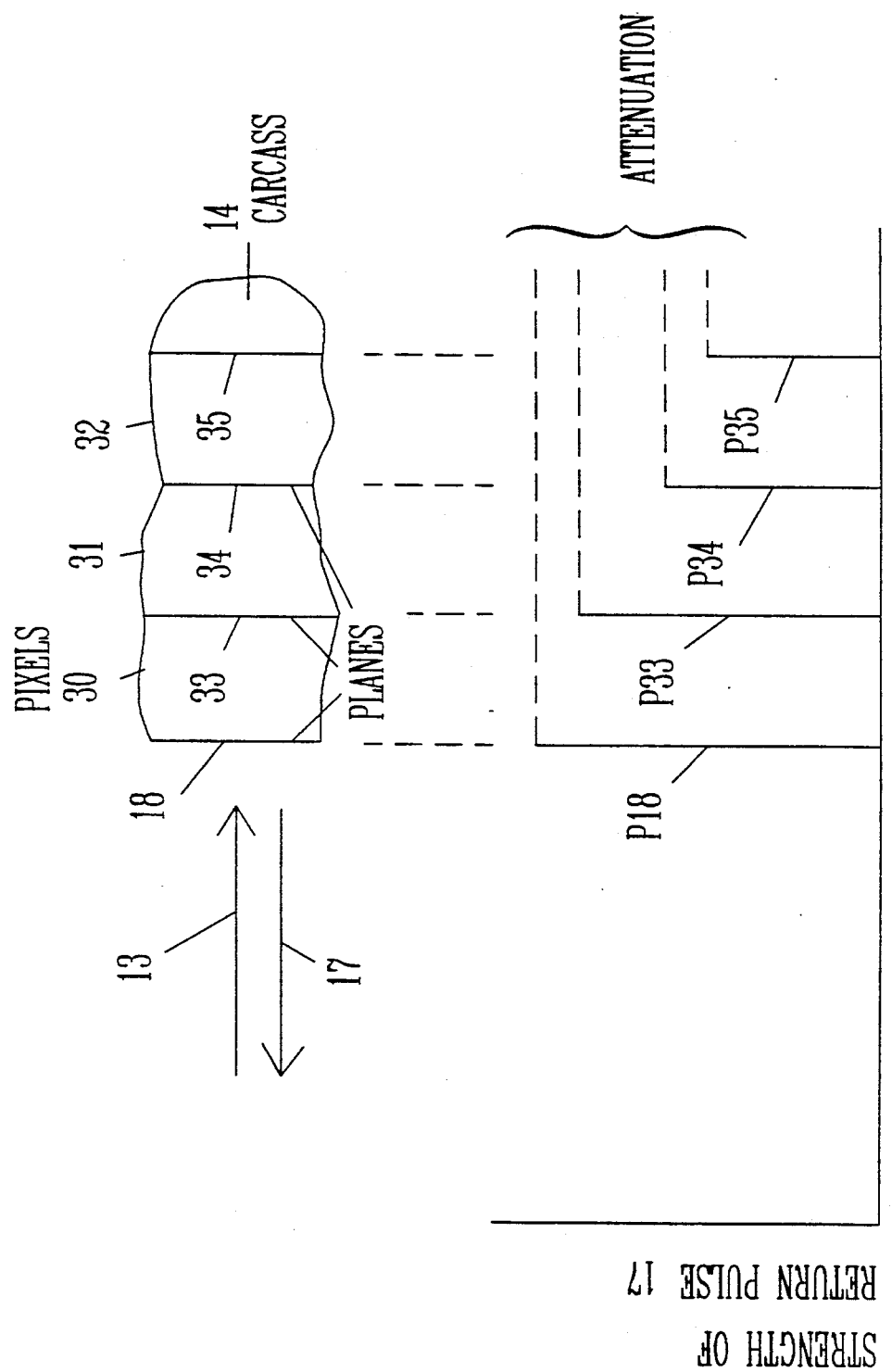
FIG. 3 is a pulse diagram.

FIG. 3 illustrates this process diagrammatically, showing a portion of the carcass 14 that is assumed to consist of a number of pixels 30, 31, 32 . . . of different materials (fat, lean etc.), and hence presenting to each transmitted pulse in the beam 13 a series of planes 18 (outer surface) and 33, 34, 35 . . . (between pixels), each of which planes will generate a corresponding return pulse P18, P33, P34, P35 . . . in the beam 17. Due to the attenuation that takes place in each pixel, each such return pulse will be weaker than its predecessor, the amount of such attenuation being determined by the thickness and nature of the pixel immediately preceding the plane from which the weaker pulse was returned. Since the thickness of each pixel is known from the time spacing of the pulses, the attenuation $\alpha$ of the pixel and hence its nature (fat, lean etc.) can be determined from the equations given above.

It will be seen that the dimensions of each pixel are thus determined by the cross section of the transmitted pulse (in the directions transverse to the pulse axis) and by the spacing between pulses (along the pulse axis).

Figure 4:
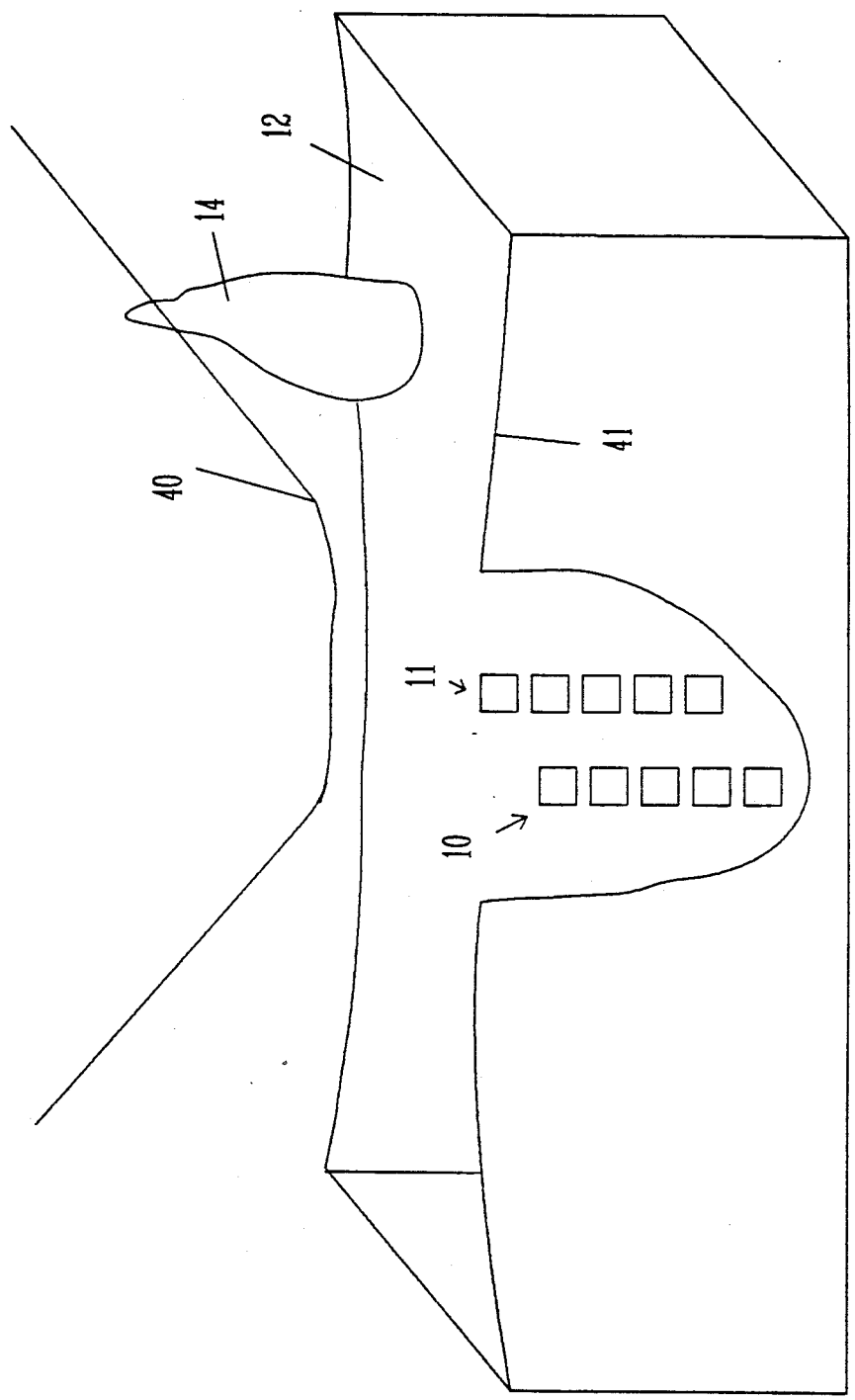
FIG. 4 is a diagrammatic, cut-away view of one form of apparatus that can be employed for moving carcasses relative to the transducers.
Figure 5:
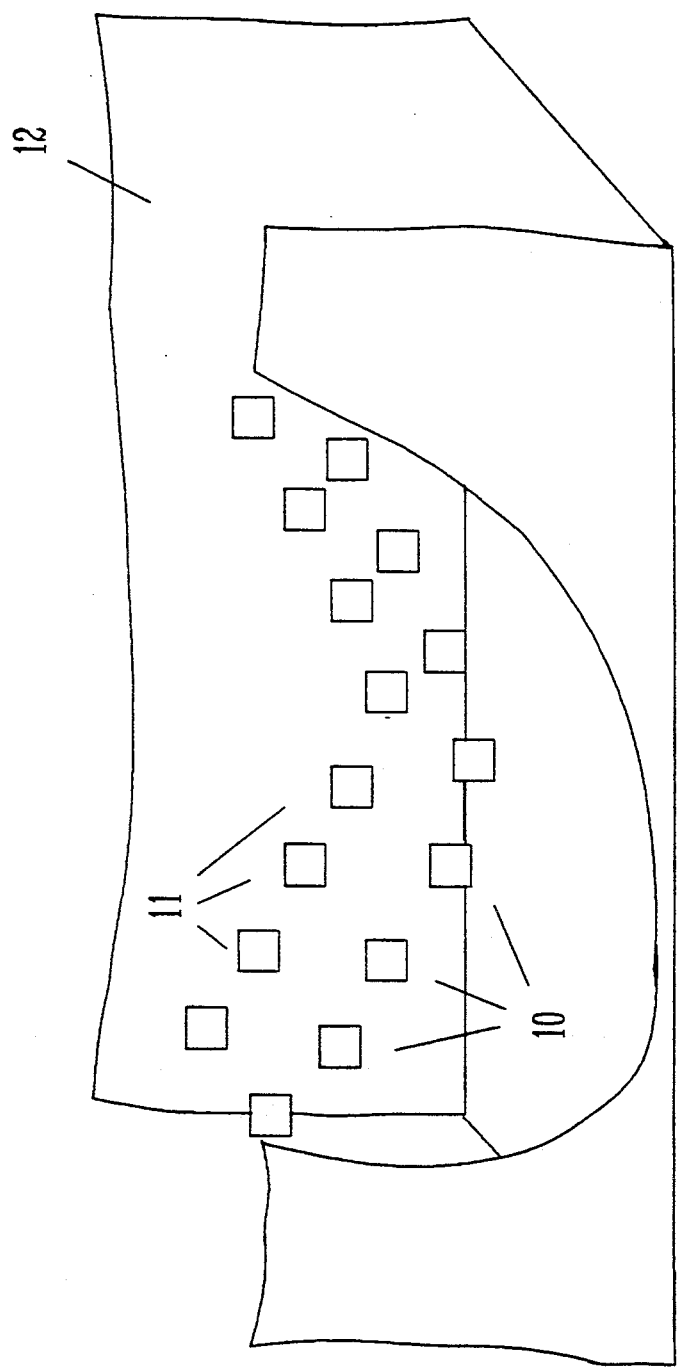
FIG. 5 is a modification of FIG. 4.

Depending on the animal carcass to be tested (whether hog, beef or lamb) and the accuracy required, one or several columns of transducers can be employed, with a larger or smaller number of transducers in each column. FIG. 4 shows one column of pairs of transducers 10 and 11 arranged in aligned pairs on opposite sides of the tank 12. The carcasses 14 are brought into the tank by an overhead conveyor 40, i.e. the moving mechanism 27. The conveyor is so arranged that each carcass is totally immersed in the water between the transducers. The narrowing of the tank at 41 is to minimise splashing and turbulence in the water caused by the carcasses entering and leaving the water. To prevent false readings, the water should be circulated and filtered of particles larger than 1 mm. The measurements can be carried out in basically two ways:

1) statically, each measurement taking place only after the carcass has been immersed and momentarily stopped (FIG. 4), being moved forward by the width of one pixel and stopped again until the entire carcass has been measured 2) dynamically, where a measurement begins immediately the lower end of the carcass reaches the water and cross-sections of the carcass are measured at prearranged intervals (FIG. 5).

Numerous different arrangements of the arrays of transducers 10 and 11 will thus be possible, along with variations in the number of pairs of transducers used.

The software handles communication between the computer 20 and the scanner 21; controls the measurements, e.g. starts and stops the timer 25; instructs the scanner 21 to measure the intensity of the return pulses; and commands the moving mechanism 27 to step to the next position etc. It also calculates the attenuation coefficients o for each pixel, and stores the data in memory; calculates the mean velocity V from the data of the timer; and calculates the ratio F. In addition it keeps the measurement process under strict control. If measurement is unsuccessful, it instructs the system to repeat the measurement.

The average cross-section of a carcass is approximately 40×40 cm. Assuming 1600 pixels per cross section, each pixel represents a 1×1 cm volume of tissue. If this accuracy is not needed, the number of pixels per cross-section can be reduced, thus decreasing the measurement time.

The software also develops the image processing routine that compiles and displays in color the attenuation values (nature of the material) of each cross-section of the carcass from the measurement data. The fat, meat and bone are displayed in different colors; any abscesses (if bigger than 4 mm) also appear.

This routine is, in simplified form, as follows:

1. Scanner selects one pulse axis, emits pulses and measures the intensity of return pulses and stores data in the memory.
2. Timer measures the time of through transmission and the timing of the return pulses and stores the data in memory.
3. The computer calculates the thickness D3 of the carcass and stores the data in memory.
4. The computer calculates the velocity V of the pulse in the carcass and stores the data in memory.
5. The computer calculates fat-to-lean ratio F of one pulse axis and stores the data in memory.
6. The computer calculates the attenuation α and the location of the pixels on the pulse axis and stores the data in memory.
7. The computer separates the pixels by the value of α and determines the material of each pixel by comparing α with the known values.
8. The computer calculates the positions and the identities of each of the pixels and stores the data in memory.
9. The foregoing routine is repeated for each other pulse axis.
10. The computer generates a three-dimensional image; calculates the overall value of the fat-to-lean ratio F; indicates if there is any abscess bigger than allowed; and calculates the total percentage of abscesses.

We claim:

1. A method of measuring the ratio of fat-to-lean in a meat carcass, comprising
   (a) immersing the carcass in a liquid,
   (b) emitting at a first location a first, focused, ultrasonic pulse, and directing said pulse through the liquid in a first direction along a first pulse axis to a first surface of the carcass,
   (c) detecting at the first location a first return pulse reflected by said surface along said axis in a second direction opposite the first direction,
   (d) measuring a time interval between the emitting and detecting steps, and calculating from the known velocity of the ultrasonic pulse in the liquid a first distance of said first surface from the first location,
   (e) emitting at a second location a second, focused, ultrasonic pulse, and directing said second pulse through the liquid in the second direction along said axis against a second surface of the carcass on the side thereof opposite the first surface,
   (f) detecting at the second location a second return pulse reflected by the second surface along said axis in the first direction,
   (g) measuring a time interval between emitting the second pulse and detecting the second return pulse, and calculating from said known velocity a second distance of said second surface from the second location,
   (h) calculating the thickness of the carcass along said axis from said calculated first and second distances and the known distance apart of the first and second locations,
   (i) detecting at the second location a third pulse resulting from transmission of the first emitted pulse through the carcass along said axis in the first direction,
   (j) measuring a time interval between emission of the first emitted pulse and detection of the third pulse, and calculating the velocity of the first emitted pulse while travelling through the carcass from said calculated first and second distances and said thickness,
   (k) calculating the ratio of fat-to-lean in the carcass along said axis from this last-mentioned velocity and the known velocities of the pulses in fat and in lean,
   (l) repeating the foregoing steps (b) to (k) while scanning the pulse axis across the carcass in directions transverse to the extent of said axis to calculate said ratio of fat-to-lean along a plurality of other pulse axes in the carcass parallel to the first pulse axis, and
   (m) combining the ratio calculations to measure the overall fat-to-lean ratio of the carcass.

2. A method according to claim 1, wherein said scanning of the pulse axis is at least in part effected by moving the carcass relative to the pulse axis.

3. A method according to claim 1, wherein said scanning of the pulse axis is at least in part effected by providing a plurality of pairs of spaced apart first and second locations whereby to provide a plurality of parallel pulse axes.

4. method of imaging the interior of a meat carcass containing pixels of different materials comprising
   (a) immersing the carcass in a liquid,
   (b) emitting at a first location a first, focused, ultrasonic pulse and directing said pulse through the liquid in a first direction along a first pulse axis to a first surface of the carcass,
   (c) detecting at said location a series of return pulses reflected respectively by said carcass surface and by successive planes between said pixels in the interior of the carcass, said return pulses travelling along said axis in a second direction opposite the first direction,
   (d) measuring relative intensities of the respective return pulses, and calculating therefrom the attenuation coefficient of each said pixel along the pulse axis to identify the nature of such pixel,
   (e) measuring a time interval between the emission of the pulse and the detection of each respective return pulse, and calculating from such time intervals the location of each said pixel along the pulse axis,
   (f) repeating the foregoing steps (b) to (e) while scanning the pulse axis across the carcass in directions transverse to the extent of said axis to obtain data on the location and identity of each pixel along a plurality of other pulse axes in the carcass parallel to the first pulse axis, and
   (g) combining such location and identity data to form a three-dimensional image of the location, shape, extent and identity of the materials constituting the carcass (fat, lean, bone, abscesses, other tissues).

5. A method according to claim 4, including (h) measuring on each pulse axis the intensity of a pulse transmitted through the carcass and received at a second location beyond a second surface of the carcass on the side thereof opposite the first surface to detect in the carcass any material having a high attenuation coefficient.

6. A method according to claim 5, including
   (i) emitting at said second location a second, focused, ultrasonic pulse and directing said second pulse through the liquid along each said pulse axis in the second direction against the second surface of the carcass,
   (j) detecting at each of the first and second locations a return pulse received from the respective first and second surfaces, measuring time intervals between the respective emitting and detecting steps, and calculating the distances of the respective surfaces from the respective locations and hence the thickness of the carcass along each pulse axis, (k) detecting at the second location a third pulse resulting from transmission of the first emitted pulse through the carcass along each pulse axis in the first direction, (l) measuring on each pulse axis a time interval between emission of the first emitted pulse and detection of the third pulse, and calculating the velocity of the first emitted pulse while travelling through the carcass, and (m) calculating the ratio of fat-to-lean in the carcass from this velocity for each pulse axis and the known velocities of the pulses in fat and in lean.

7. A method according to any one of claims 4 to 6, wherein said scanning of the pulse axis is at least in part effected by moving the carcass relative to the pulse axis.

8. A method according to any one of claims 4 to 6, wherein said scanning of the pulse axis is at least in part effected by providing a plurality of pairs of spaced apart first and second locations whereby to provide a plurality of parallel pulse axes.

9. A method according to any one of claims 4 to 6, wherein said step (d) of determining the attenuation coefficient of each pixel from the relative intensities of the respective return pulses is conducted in accordance with the equation $$\alpha \propto \frac{\log I(d_1) - \log I(d_2)}{d_2 - d_1}$$

where
$d_1$ is the distance into the carcass from the surface thereof along the pulse axis of a first plane between a first pair of said pixels,
$d_2$ is the distance into the carcass from the surface thereof along the pulse axis of a second plane between a second pair of said pixels,
$I(d_1)$ is the intensity of the return pulse received from the first plane,
$I(d_2)$ is the intensity of the return pulse received from the second plane, and
$\alpha$ is the attenuation coefficient of the material between the first and second planes.

10. Apparatus for measuring the ratio of fat-to-lean in a meat carcass, comprising (a) a bath for containing a liquid,
(b) at least one pair of ultrasonic transducers mounted on opposite sides of said bath facing and aligned with each other to define a pulse axis, each transducer having means for emitting a focused, ultrasonic pulse along said axis through the liquid and for detection of a reflected or transmitted pulse,
(c) means for measuring time intervals
  (i) between emission of a pulse by one of said transducers and detection thereby of a corresponding return pulse reflected from a surface of the carcass immersed in the liquid between the transducers, and
  (ii) between emission of a pulse by one of said transducers and detection by the other transducer of a corresponding pulse transmitted through the carcass, and
(d) means for calculating from said time intervals the velocity of the pulse in the carcass and means for calculating from said velocity said fat-to-lean ratio along said pulse axis from the known velocity of the pulse in lean and the known velocity of the pulse in fat.

11. Apparatus according to claim 10, comprising
(e) a plurality of said aligned pairs of transducers for defining a plurality of pulse axes,
(f) means for scanning said pairs of transducers to calculate said fat-to-lean ratio along each of said pulse axes, and
(g) means for combining such fat-to-lean ratios to measure the overall fat-to-lean ratio of the carcass.

12. Apparatus according to claim 10 or 11, including means for moving the carcass relative to each pair of transducers.

13. Apparatus for identifying the nature of portions of the interior of a meat carcass containing pixels of different materials, comprising
(a) a bath for containing a liquid,
(b) a primary ultrasonic transducer mounted on a first side of said bath for emitting a focused, ultrasonic pulse along a pulse axis through the liquid and into a carcass immersed in the liquid and for detecting a series of return pulses reflected respectively by a surface of the carcass and by successive planes between said pixels in the interior of the carcass,
(c) means for measuring time intervals between emission of a pulse by said transducer and detection of each said return pulse by said transducer,
(d) means for calculating from such time intervals the location of each said pixel along the pulse axis,
(e) means for measuring the relative intensities of each said return pulse detected by the transducer, and
(f) means for calculating from such relative intensities the attentuation coefficient of each said pixel along the pulse axis to identify the nature of such pixel.

14. Apparatus according to claim 13, comprising
(g) a plurality of said transducers mounted on said first side of the bath for respectively defining each of a plurality of different pulse axes,
(h) means for scanning said transducers to identify the nature of each said pixel along each said pulse axis, and
(i) means for combining the location and identity of each said pixel along each said axis to provide a three-dimensional image of the location, shape and nature of the interior of the carcass.

15. Apparatus according to claim 13 or 14, including means for moving the carcass relative to each transducer.

16. Apparatus according to claim 13 or 14, including a further ultrasonic transducer aligned with the or each said primary transducer to form at least one pair of cooperating transducers, the further transducer of each pair including means for detecting a pulse transmitted by the primary transducer of the pair through the liquid and the carcass, and means for measuring the intensity of such detected transmitted pulse for detecting the presence in the carcass of a material having a high attenuation coefficient.

17. Apparatus for measuring the ratio of fat-to-lean in a meat carcass and for generating an image of the location, shape and nature of pixels of different materials in the interior of the carcass, comprising
(a) a bath for containing a liquid, (b) means for immersing a carcass in said liquid and for moving the carcass relative to the bath, (c) a plurality of pairs of cooperating ultrasonic transducers, the transducers of each pair being mounted on opposite sides of the bath from each other and being aligned with each other to define a pulse axis, the pulse axes of the respective pairs of transducers being parallel with each other, each transducer having means for emitting a focused, ultrasonic pulse for transmission through the liquid and the carcass, and for detecting a pulse so transmitted or reflected by the carcass, (d) means for measuring time intervals
   (i) between emission of a pulse by one of said transducers and detection of return pulses reflected respectively from surfaces of the carcass and from planes between pixels in the interior of the carcass, and
   (ii) between a pulse transmitted from one transducer to the other transducer of the pair through the carcass, (e) means for calculating from such time intervals the location of each pixel and the fat-to-lean ratio along each pulse axis, (f) means for measuring the relative intensities of said return pulses, (g) means for calculating from such relative intensities the attenuation coefficient of each said pixel along each pulse axis to identify the nature of said pixel, said calculating means including means for solving the equation $$\alpha \propto \frac{\log I(d_1) - \log I(d_2)}{d_2 - d_1}$$

where
   $d_1$ is the distance into the carcass from the surface thereof along each pulse axis of a first plane between a first pair of said pixels, $d_2$ is the distance into the carcass from the surface thereof along each pulse axis of a second plane between a second pair of said pixels,
   $I(d_1)$ is the intensity of the return pulse received from the first plane,
   $I(d_2)$ is the intensity of the return pulse received from the second plane, and
   $\alpha$ is the attenuation coefficient of the measured pixel between the first and second planes, (h) means for scanning the transducers and for actuating the carcass moving means to cause substantially the entire carcass to be penetrated by a pulse axis, and (i) means for combining the data calculated by said measuring and calculating means to measure the overall ratio of fat-to-lean in the carcass and to compile a three dimensional image of the location, shape and nature of the different materials in the interior of the carcass.

* * * * *